United States Patent [19]

Rane et al.

[11] Patent Number: 4,695,579

[45] Date of Patent: Sep. 22, 1987

[54] ANTIFUNGAL 2-AZOLYLMETHYL-3-DIFLUOROBENZYLOXY-2,3-DIHYDROFLUORO-BENZO(B)THIOPHENS

[75] Inventors: Dinanath F. Rane, Sayreville; Jagdish A. Desai, Parlin; Russell E. Pike, Stanhope, all of N.J.

[73] Assignee: Schering Corporation, Kenilworth, N.J.

[21] Appl. No.: 684,872

[22] Filed: Dec. 21, 1984

[51] Int. Cl.[4] .................. A61K 31/415; A61K 31/41; C07D 409/06

[52] U.S. Cl. .................................. 514/397; 514/383; 548/262; 548/330

[58] Field of Search ............... 548/336, 262; 514/383, 514/398, 397

[56] References Cited

U.S. PATENT DOCUMENTS

| | | | |
|---|---|---|---|
| 4,352,808 | 10/1982 | Rane et al. | 514/314 |
| 4,431,816 | 2/1984 | Rane et al. | 548/336 |
| 4,468,404 | 8/1984 | Rane et al. | 514/253 |

OTHER PUBLICATIONS

Loebenberg, D., et al., *Abstracts, Interscience Conference in Antimicrobial Agents and Chemotherapy*, 1982, Abstract No. 474.

Lennette, E., et al., *Manual of Chemical Microbiology*, American Society for Microbiology, New York, 1980, pp. 648–649.

*Primary Examiner*—Richard A. Schwartz
*Attorney, Agent, or Firm*—Thomas D. Hoffman; Gerald S. Rosen

[57] ABSTRACT

2-Azolylmethyl-3-difluorobenzyloxy-2,3-dihydro-5- and 6-fluorobenzo[b]thiophen antifungally compounds, especially 2-(1H-imidazolylmethyl-3-(2',6'-difluorobenzyloxy)-2,3-dihydro-5-fluorobenzo[b]thiophene, pharmaceutical compositions containing them and their use in treating fungal infections in animals including humans are disclosed.

17 Claims, No Drawings

ANTIFUNGAL 2-AZOLYLMETHYL-3-DIFLUOROBENZYLOXY-2,3-DIHYDROFLUORO-BENZO(B) THIOPHENS

BACKGROUND OF THE INVENTION

This invention relates to 2-azolylmethyl-3-difluorobenzyloxy-2,3-dihydro-5-and-6-fluorobenzo[b]-thiophene, antifungal compounds, pharmaceutical compositions containing them, and their use in treating fungal infections in animals, including humans.

U.S. Pat. No. 4,352,808 (Rane et al.) and the corresponding European patent application EP No. 54,233 disclose 3-aralkyloxy-2,3-dihydro-2-(1H-imidazolylmethyl)benzo b]thiophene antifungal compounds.

U.S. Pat. No. 4,431,816. (Rane et al.) discloses 3-hydroxy-2,3-dihydro-2-(1H-imidazolylmethyl)benzo[b]thiophene antifungal compounds. U.S. Pat. No. 4,468,404 discloses 3-arylalkoxy-2,3-dihydro-2-(1H-1,2,4-triazolymethyl)benzo[b]thiophene antifungal compounds. While U.S. Pat. Nos. 4,352,808 and 4,468,404 disclose antifungal compounds that are generic to the compounds of this invention, there is no specific disclosure of the compound this invention and no indication that the trifluoro compounds of this invention would be expected to have properties superior compared to the trichoro-compounds, e.g., cis-5-chloro-3-(2',6'-dichlorobenzyloxy)-2,3-dihydro-2-(1H-imidazolymethyl)benzo[b] thiophene specifically disclosed in the above-identified U.S. patents.

SUMMARY OF THE INVENTION

The compounds of this invention are represented by the following formula I

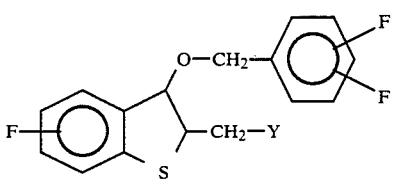

or a pharmaceutically acceptable acid salts thereof, wherein Y is imidazolyl, 1,2,4-triazolyl or lower alkyl and aryl substituted derivatives thereof, said aryl being a memeber selected from the group consisting of phenyl, halophenyl; and lower alkylphenyl; in racemic or optically active form.

The present invention also provides a pharmaceutical composition comprising an antifungally effective amount of a compound represented by formula I or a pharmaceutically acceptable acid salt thereof, together with a pharmaceutically acceptable carrier or diluent.

The present invention further provides a method of treating susceptible fungal infections which comprises administering to a host in need of such treatment an antifungally effective amount of a compound represented by formula I or a pharmaceutically acceptable acid salt thereof, in racemic or optically active form, or a pharmaceutical composition comprising such a compound and a pharmaceutically acceptable carrier or diluent.

A preferred method aspect of the present invention is a method of treating susceptible fungal infections which comprises administering to a host in need of such treatment an antifungally effective amount of cis-2-(1H-imidazolylmethyl)-3-(2',6'-difluorobenzyloxy)-2,3-dihydro-5-fluorobenzo[b]thiophene or a pharmaceutical composition comprising said compound and a pharmaceutically acceptable carrier or diluent.

The most preferred compound of the present invention is cis-2-(1H-imidazolylmethyl)-3-(2',6'-difluorobenzyloxy)-2,3-dihydro-5-fluorobenzo[b]thiophene or a pharmaceutically acceptable acid salt thereof, e.g. HCl.

The preferred pharmaceutical composition of the present invention comprises an antifungally effective amount of cis-2-(1H-imidazolymethyl)-3-(2',6'-difluorobenzyloxy-2,3-dihydro-5-fluorobenzo[b]thiophene or a pharmacetucially acceptable acid salt thereof together with a pharmaceutically acceptable carrier or diluent.

DETAILED DESCRIPTION OF THE INVENTION AND THE PREFERRED EMBODIMENTS

As used in the specification and claims, the term "lower alkyl" refers to straight and branched chain alkyl groups of 1 to 6 carbon atoms, such as methyl, ethyl, n- and iso-propyl, n-, sec- and tert-butyl, n-, sec-, tert-pentyl and n-, sec- and tert-hexyl. By the term "aryl" as used herein is meant phenyl and halophenyl, i.e., phenyl substituted by 1 to 3 halogens (especially fluorine or chlorine) e.g., mono-, di- and trihalophenyl or loweralkyl phenyl, i.e., phenyl substituted by 1 to 3 lower alkyl groups, mono-, di- and triloweralkyl phenyl, such as 4-chloro- or 4-fluorophenyl, 2,4-dichloro- or 2,4-difluorophenyl, 2,5-dichloro or 2,5-difluorophenyl and 2,6-dichloro- or 2,6-difluorophenyl and 2,4,6-trichloro- or 2,4,6-trifluorophenyl.

Compounds of the present invention can exist in two isomeric forms, i.e.,($\pm$)-cis-2,3 and($\pm$)-trans-2,3. Both forms (each racemic mixtures) are within the scope of the present invention, as are the individual optical isomers e.g., ($\pm$)- or (-)-cis-2,3 isomers of formula I.

The compounds of the present invention may be prepared by reacting a compound of formula II with a difluorobenzyl halide in the presence of aqueous base in an organic solvent, e.g., 50% NaOH in tetrahydrofuran/water and in the presence of a suitable phase-transfer agent, or catalyst e.g., N,N,N- tricaprylyl-N-methylammonium chloride at 0-30° C. for 1-4 hrs.

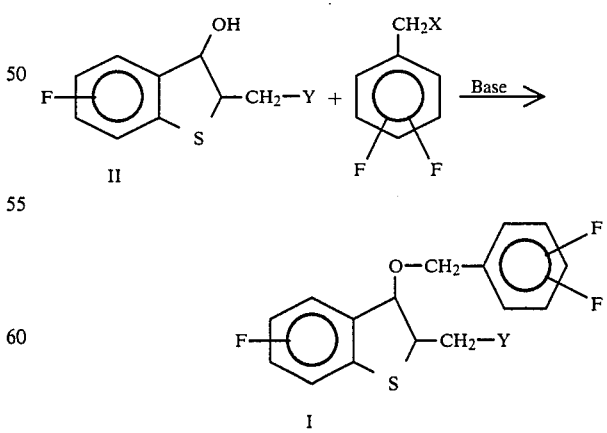

(X = e.g., Br or Cl)

Other phase-transfer catalysts useful for the invention are disclosed in Aldrichimica Acta, 9,35 (1976) and also U.S. Pat. No. 3,992,432.

The product is isolated and purified in a conventional manner, e.g., by column chromatography. The most preferred compound of the present invention cis-2-(1H-imidazolylmethyl-3-(2',6'-difluorobenzyloxy)-2,3-dihydro-5-fluorobenzo[b]thiophene, was prepared in this manner from cis-2,3-dihydro-2-(1H-imidazolymethyl)-3-hydroxy-5-fluoro benzo[b]thiophene and 2,6-difluorobenzyl chloride. Compounds of formula II are prepared in accordance with the procedures of U.S. Pat. No. 4,352,808, 4,318,816 and 4,468,404. The difluorobenzyl halides, e.g., chlorides or bromides are commerically available.

The compounds of this invention exhibit broad spectrum antifungal activity, in conventional antifungal screening tests, against human and animal pathogens, such as the following: Aspergillus, Candida, Geotrichum, Microsporum, Monosporium, Rhodotorula, Saccharomyces, Trichophyton, and Torulopsis. In Sabourand broth medium, the most prefered compound of this invention, cis-2-(1H-imidazolylmethyl)-3-(2',6'-difluorobenzyloxy)-2,3-dihydro-5-fluorobenzo[b]thiophene had a mean Minimum Inhibitory Concentration (MIC) of 15 mcg/mL in a 48 hour test; the MIC of this compound against Candida parapsilosis ,Trichophyton rubrum and Geotrichum candidum was ≦0.031 mcg/mL after 48 hours, and against Saccharomyces cerevisiae and Monosporium apiospermum was 0.125 mcg/mL after 48 hours and against various other strains of Candida was 32.0 mcg/mL after 48 hours. In Eagles medium, the mean MIC for the most prefered compound of this invention against six strains of Candida was 0.36 mcg/mL after 48 hours.

The compounds of this invention also exhibited superior topical antifungal activity in in-vivo tests in animals compared to miconazole and clotrimazole, present commercial antifungal products. For example, in a hamster vaginal Candida C-60 topical infection model, the percent inhibition of infection for the most preferred compound of this invention was superior to those of miconazole and clotrimazole; in the guinea pig Trichophyton dermatophyte topical infection model, the percent inhibiton of infection for the most preferred compound of this invention was superior to that of miconazole.

The present invention also provides a pharmaceutical composition comprising an effective antifungal amount of a compound represented by formula I or a pharmaceutically acceptable salt thereof and a pharmaceutically acceptable carrier or diluent.

The preferred pharmaceutically acceptable salts are nontoxic acid addition salts formed by adding to the compound of the present invention about a stoichiometric amount of a mineral acid, such as HCl, HBr, $H_2SO_4$ or $H_3PO_4$ or of an organic acid, such as acetic, propionic, valeric, oleic, palmitic, stearic, lauric, benzoic, lactic, para-toluene sulfonic, methane sulfonic, citric, maleic, fumaric, succinic and the like, respectively.

The pharmaceutical compositions of the present invention may be formulated by combining the compound of this invention or a pharmaceutically acceptable salt thereof with any suitable, i.e., inert, pharmaceutical carrier or diluent adapted for administration orally, parentally or topically in a variety of formulations. The preferred mode of administration is topical.

Examples of suitable compositions include solid or liquid compositions for oral administration such as tablets, capsules, pills, powders, granules, solutions, suspensions or emulsions. They may also be manufactured in the form of sterile solid compositions which can be dissolved in sterile water, physiological saline or some other sterile injectable medium immediately before use.

Topical dosage forms may be prepared according to procedures well known in the art, and may contain a variety of ingredients excipients and additives. The formulations for topical use include ointments, creams, lotions, powders, aerosols, pessaries and sprays. Of these, ointments, lotions and creams may contain water, oils, fats, waxes, polyesters, alcohols, or polyols, plus such other ingredients as fragrances, emulsifiers and preservatives. Powders are made by mixing the active ingredient with a readily available, inert, pulverous distributing agent, such as talcum, calcium carbonate, tricalcium phosphate, or boric acid. Aqueous suspensions of the above powders may also be made. Solutions or emulsions may also be prepared using inert solvents which are preferably nonflammable, odorless, colorless and nontoxic, for example, vegetable oils, isopropanol, dimethyl sulfoxide, hydrogenated naphthalenes, and alkylated naphthalenes. Similarly, aerosol or non-aerosol sprays may be prepared using solutions or suspensions in appropriate solvents, e.g., difluorodichloromethane, for aerosols.

Parenteral forms to be injected intravenously, intramuscularly, or subcutaneously are usually in the form of a sterile solution, and may contain salts or glucose to make the solution isotonic.

Based on the greater in vivo topical activity for the compound of this invention compared to miconazole, the dosage of the compound of the present invention employed to combat a given fungal infection in animals, e.g., mammals, including humans be generally somewhat less than the dosage requirements of present commercial products such as miconazole.

It will be appreciated that the actual preferred dosages of the compound of the present invention or pharmaceutically acceptable salts thereof will vary according to the particular composition formulated, the mode of application and the particular situs, host and disease being treated. Many factors that modify the action of the drug will be taken into account by the attending clinician, e.g., age, body weight, sex, diet, time of administration, rate of excretion, condition of the host, drug combinations, reaction sensitivities and severity of the disease. Administration can be carried out continuously or periodically within the maximum tolerated dose. Optimal application rates for a given set of conditions can be readily ascertained by the attending clinician using conventional dosage determination tests.

In general, the dosage for man ranges from about 50 mg per day to about 800 per day, with about 100 mg to 400 mg per day in single or divided doses being preferred.

The following Examples illustrate the invention.

EXAMPLES

PREPARATION 1

(±)-CIS-2-(1H-IMIDAZOLYLMETHYL)-3-HYDROXY-2,3-DIHYDRO-5-FLUOROBENZO[b]-THIOPHENE

The procedure of Preparation 1 of U.S. Pat. No. 4,352,808, which is hereby incorporated by reference, is followed except that an equivalent quantity of 6-fluoro-thiocoumaran-4-one hydrochloride is substituted for 7-chloro-thiocoumaran-3-one hydrochloride to give the title compound m.p. 182°–184° C.

PREPARATION 2

(±)-CIS-2-(1H-IMIDAZOLYLMETHYL)-3-HYDROXY-2,3-DIHYDRO-6-FLUOROBENZO[b]-THIOPHENE

The procedure of Preparation 1 of U.S. Pat. No. 4,352,808 is followed except that an equivalent quantity of 7-fluorothiochroman-4-one is substituted for 7-chlorothiochroman-4-one to give the title compound, m.p. 165°–166° C.

PREPARATION 3

(±)-CIS-2-(1H-1,2,4-TRIAZOLYLMETHYL)-3-HYDROXY-2,3-DIHYDRO-5-FLUOROBENZO[b]-THIOPHENE AND CIS-2-(1H-1,2,4-TRIAZOLYLMETHYL)-3-HYDROXY-2,3-DIHYDRO-6-FLUOROBENZO[b]-THIOPHENE

The procedures of Preparation 1 and 2 are followed except that an equivalent quantity of 1,2,4triazole is substituted for imidazole to give the title compounds.

EXAMPLE 1

(±)-CIS-2-(1H-IMIDAZOLYLMETHYL)-3-(2',6'-DIFLUOROBENZYLOXY)-2,3-DIHYDRO-5-FLUOROBENZO[b]THIOPHENE

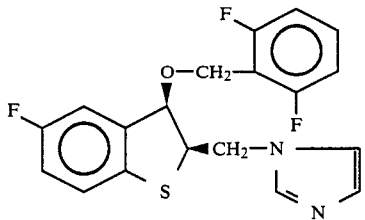

2.5 g(10 mmole) of (±)-cis-2,3-dihydro-5-fluoro-3-hydroxy-2-(1H-imidazolymethyl)benzo[b]thiophene, 3.10 g (15 mmole) of 2,6-difluorobenzylbromide (Aldrich Chemical Co.), and 3 drops of methyltricaprylylammonium chloride were stirred in 25 mL of 50% NaOH and 50 mL of THF at RT for 1 hr. The reaction mixture was poured into 500 mL of $HCCl_3$ with another 500 mL of $H_2O$. The $HCCl_3$ was dried over anhydrous $MgSO_4$ and removed the $CHCl_3$ in vacuo. The residue was chromatographed on silica gel eluting with $CHCl_3$ followed by recrystallization from cyclohexane to give 2.36 g, m.p. 167°–168°, of (±)-cis-3-(2',6'-difluorobenzyloxy)-2,3-dihydro-5-fluoro-2-(1H-imidazolylmethyl)benzo[b]thiophene: Calculated: C,60.63; H,4.02; N,7.44; F,15.14; S,8.52. Found: C,60.73; H,3.99; N,7.17; F,15.08; S,8.55; $^1H$ nmr (200 MHZ, $CDCl_3$) δ: 4:04 (m, 2H, 4.49 (m,1H), 4.85 (bs, 2H), 5.16 (d, 1H, J=5.0), 6.93 (bs, 1H), 7.05 (bs, 1H), 7.50 (bs, 1H) and 6.95–7.4 (m, 6H).

EXAMPLE 2

(±)-cis-2-(1H-1,2,4-Triazolymethyl)-3-Difluorobenzyloxy -2,3-Dihydro-5-Fluorobenzo[b]Thiophenes and (±)-cis-2-(1H-1,2,4-Triazolylmethyl)-3-Difluorobenzyloxy)-2,3-Dihydro-6-Fluorobenzo[b]Thiophenes The procedure of Example 1 is followed except that equivalent quantities of the title compounds of Preparation 3 are substituted for cis-2,3-dihydro-5-fluoro-3-hydroxy-2-(1H-imidazolylmethyl)benzo[b]thiophene and equivalent quantities of 2,4- and 2,5-difluorobenzyl bromide (of Preparation 5) are substituted for 2,6-difluorobenzyl bromide to give:
(a)   (±)-cis-2-(1H-1,2,4-triazolylmethyl)-3-(2',4'-difluorobenzyloxy)-2,3-dihydro-5-fluorobenzo[b]thiophene;
(b)   (±)-cis-2-(1H-1,2,4-triazolylmethyl)-3-(2',4'-difluorobenzyloxy)-2,3-dihydro-6-fluorobenzo-[b]thiophene;
(c)   (±)-cis-2-(1H-1,2,4-triazolylmethyl)-3-(2',5'-difluorobenzyloxy)-2,3-dihydro-5-fluorobenzo[b]thiopene; and
(d)   (±)-cis-2-(1H-1,2,4-triazolylmethyl)-3-(2',5'-difluorobenzyloxy)-2,3-dihydro-6-fluorobenzo[b]thiophene The corresponding (±)-trans compounds are prepared by using the (±)-trans isomers corresponding to the above listed (±)-cis isomers in Example 2.

EXAMPLE 3

(±)-cis-2-(1H-Imidazolylmethyl)-3-Difluorobenzyloxy-2,3-Dihydro-5-Fluorobenzo[b]Tiophenes The procedure of Example 1 is followed except that equivalent quantites of 2,3-difluorobenzyl bromide-2,4-difluorobenzyl bromide and 2,5-difluorobenzyl bromide are substituted for 2,6-difluorobenzyl bromide to give:
(a)   (±)-cis-2-(1H-imidazolylmethyl)-3-(2',3'-difluorobenzyloxy)-2,3-dihydro-5-fluorobenzo[b]thiophene;
(b)   (±)-cis-2-(1H-imidazolylmethyl)-3-(2',4'-difluorobenzyloxy)-2,3-dihydro-5-fluorobenzo[b]thiophene; and
(c)   (±)-cis-2-(1H-imidazolymethyl)-3-(2',5'-difluorobenzyloxy)-2,3-dihydro-5-fluoro[b]thiopene.

The corresponding (±)-trans compounds are prepared by using the trans isomers corresponding to the above listed cis isomers in Example 3.

EXAMPLE 4

(±)-cis-2-(1H-Imidazolylmethyl)-3-Difluorobenzyloxy-2,3-Dihydro-6-Fluorobenzo[b]Thiophene The procedure of Example 1 is followed except that about 1.5 mmoles of 2,3-difluorobenzylbromide, 2,4-difluorobenzyl bromide, 2,5-difluorobenzyl bromide and 2,6-difluorobenzyl bromide are reached with about 1 mmole of (±)-cis-2-(1H-imidazolymethyl)-3-hydroxy-2,3-dihydro-6-fluorobenzo[b]thiophene to give:
(a)   (±)-cis-2-(1H-imidazolylmethyl)-3-(2',3'-difluorobenzyloxy)-2,3-dihydro-6-fluorobenzo[b]thiophene;
(b)   (±)-cis-2-(1H-imidazolylmethyl)-3-(2',4'-difluorobenzyloxy)-2,3-dihydro-6-fluorobenzo[b]thiophene;
(c)   (±)-cis-2-(1H-imidazolymethyl)-3-(2',5'-difluorobenzyloxy)-2,3-dihydro-5-fluoro[b]thiopene; and
(d)   (±)-cis-2-(1H-imidazolylmethyl)-3-(2',6'-difluorobenzyloxy)-2,3-dihydro-6-fluoro[b]thiopene.

The corresponding (±)-trans isomers are prepared by using the (±)-trans isomers corresponding to the above listed (±)-cis isomers in Example 4.

EXAMPLE 5

The following are typical pharmaceutical formulations containing as the active ingredient (designated "Drug") a compound of this invention, e.g., cis-2-(1H-imidazolylmethyl)-3-(2',6'-difluorobenzyloxy)-2,3-dihydro-5-fluorobenzo[b]thiopene. It will be appreciated, however, that this preferred compound may be replaced by equally effective quantities of the other compounds of this invention represented by formula I.

FORMULATION 1
Tablet 125.00 mg. tab.

| | |
|---|---|
| Drug | 125.00 mg. |
| Polyethylene glycol 6000 | 100.00 mg. |
| Sodium lauryl sulfate | 6.25 mg. |
| Corn starch | 30.00 mg. |
| Lactose, anhydrous | 87.25 mg. |
| Magnesium stearate | 1.50 mg. |

Procedure:

Heat the polyethylene glycol 6000 to 70°–80° C. Mix the drug, sodium lauryl sulfate, corn starch, and lactose into the liquid and allow the mixture to cool. Pass the solidified mixture through a mill. Blend granules with magnesium stearate and compress into tablets.

FORMULATION 2
Capsule 250 mg. tab.

| | |
|---|---|
| Drug | 250.00 mg. |
| Lactose, anhydrous | 100.00 mg. |
| Corn starch | 50.00 mg. |
| Microcrystalline cellulose | 95.00 mg. |
| Magnesium stearate | 5.00 mg. |

Procedure:

Mix the first four ingredients in a suitable mixer for 10–15 minutes. Add the magnesium stearate and mix for 1–3 minutes. Fill the mixture into suitable two-piece hard gelatin capsules using an encapsulating machine.

We claim:

1. A compound represented by the following formula I:

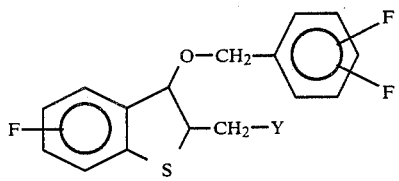

or a pharmaceutically acceptable acid salt thereof, wherein Y is imidazolyl, 1,2,4-triazolyl or lower alkyl and aryl substituted derivatives thereof, said aryl being a member selected from the group consisting of phenyl, halophenyl; and lower alkylphenyl;

in racemic or optically active form.

2. A compound of claim 1 wherein Y is imidazolyl.

3. The cis-isomer of a compound a claim 1.

4. A compound of claim 3 which is cis-2-(1H-imidazolylmethyl)-3-(2',6'-difluorobenzyloxy)-2,3-dihydro-5-fluorobenzo[b]thiophene.

5. A compound of claim 3 which is cis-2-(1H-imidazolylmethyl)-3-(2',4'-difluorobenzyloxy)-2,3-dihydro-5-fluorobenzo[b]thiophene.

6. A compound of claim 3 which is cis-2-(1H-imidazolylmethyl)-3-(2',5'-difluorobenzyloxy)-5-fluorobenzo[b]thiophene.

7. A compound of claim 3 which is cis-2-(1H-imidazolylmethyl)-3-(2',6'-difluorobenzyloxy)-2,3-dihydro-6-fluorobenzo[b]thiophene.

8. A compound of claim 1 which is trans-2-(1H-imidazolylmethyl)-3-(2',6'-difluorobenzyloxy)-2,3-dihydro-5-fluorobenzo[b]thiophene.

9. A pharmaceutical composition comprising an antifungally effective amount of a compound of claim 1 and a pharmaceutically acceptable carrier or diluent.

10. The composition of claim 9 adapted for topical administration.

11. The composition of claim 9 adapted for oral administration.

12. The composition of claim 9 adapted for parenteral administration.

13. A method of treating susceptible fungal infections which comprises administering to a host in need of such treatment an antifungally effective amount of a compound of claim 1 or a pharmaceutical composition comprising such a compound and a pharmaceutically acceptable carrier or diluent.

14. The method of claim 13 wherein the route of administration is topical.

15. The method of claim 13 wherein the route of administration is oral.

16. The method of claim 13 wherein the route of administration is parenteral.

17. The method of claim 13 wherein said compound is cis-2-(1H-imidazolylmethyl)-3-(2',6'-difluorobenzyloxy)-2,3-dihydro-5-fluorobenzo[b]thiophene or a pharmaceutical composition comprising said compound and a pharmaceutically acceptable carrier or diluent.

* * * * *